United States Patent
Morikazu et al.

(10) Patent No.: US 10,553,490 B2
(45) Date of Patent: Feb. 4, 2020

(54) PROCESSING METHOD FOR WAFER

(71) Applicant: DISCO CORPORATION, Tokyo (JP)

(72) Inventors: Hiroshi Morikazu, Tokyo (JP); Noboru Takeda, Tokyo (JP)

(73) Assignee: DISCO CORPORATION, Tokyo (JP)

(*) Notice: Subject to any disclaimer, the term of this patent is extended or adjusted under 35 U.S.C. 154(b) by 0 days.

(21) Appl. No.: 15/900,247

(22) Filed: Feb. 20, 2018

(65) Prior Publication Data
US 2018/0240708 A1  Aug. 23, 2018

(30) Foreign Application Priority Data

Feb. 21, 2017  (JP) .................. 2017-030025

(51) Int. Cl.
*H01L 21/304* (2006.01)
*H01L 21/78* (2006.01)
*H01L 21/687* (2006.01)
*G01N 29/06* (2006.01)

(52) U.S. Cl.
CPC ......... *H01L 21/78* (2013.01); *G01N 29/0654* (2013.01); *H01L 21/304* (2013.01); *H01L 21/68714* (2013.01); *G01N 2291/2697* (2013.01)

(58) Field of Classification Search
CPC . H01L 21/78; H01L 21/681; H01L 21/67288; H01L 21/304; H01L 21/3043; H01L 22/20; G01N 2291/2697; G01N 29/0654; G01N 21/9505
See application file for complete search history.

(56) References Cited

U.S. PATENT DOCUMENTS

| | | | | |
|---|---|---|---|---|
| 2015/0303113 A1* | 10/2015 | Sekiya | ............... | H01L 21/3043 438/462 |
| 2016/0284611 A1* | 9/2016 | Sekiya | ................... | H01L 22/20 |
| 2017/0045448 A1* | 2/2017 | Lin | ........................ | G01N 21/59 |
| 2017/0372908 A1* | 12/2017 | Shigematsu | ........ | H01L 21/3043 |

FOREIGN PATENT DOCUMENTS

| | | | |
|---|---|---|---|
| JP | 11176771 A | | 7/1999 |
| JP | 2015050226 A | * | 3/2015 |

* cited by examiner

*Primary Examiner* — Latanya N Crawford
(74) *Attorney, Agent, or Firm* — Greer, Burns & Crain Ltd.

(57) ABSTRACT

A processing method for a wafer including a crack detection step for irradiating illumination of a wavelength transparent to wafer, picking up an image of the wafer, and detecting whether a crack is generated within the wafer, a crack direction verification step for verifying, when a crack is detected, to which one of the first and second directions a direction in which the crack extends is nearer, a first cutting step for positioning the cutting blade to a scheduled division line of a direction decided to be a direction farther from the direction in which the crack extends from between the first and second directions and cutting the scheduled division line, and next a second cutting step for positioning the cutting blade to a scheduled division line of a direction decided to be nearer to the direction in which the crack extends and cutting the scheduled division line.

14 Claims, 3 Drawing Sheets

PROCESSING METHOD FOR WAFER

BACKGROUND OF THE INVENTION

Field of the Invention

The present invention relates to a processing method for dividing a wafer having a plurality of devices formed on a surface thereof and partitioned by scheduled division lines into individual devices.

Description of the Related Art

A wafer having a plurality of devices such as integrated circuits (ICs) or large-scale integrations (LSIs) formed on a surface thereof and partitioned by scheduled division lines is divided into individual device chips by a dicing apparatus. The divided device chips are utilized in electric apparatus such as portable telephone sets or personal computers.

The dicing apparatus can be configured from a cutting apparatus that positions a cutting blade to a scheduled division line of a wafer held on a chuck table, rotates the cutting blade and feeds the chuck table for processing to cut the scheduled division line with high accuracy (for example, refer to Japanese Patent Laid-Open No. Hei 11-176771).

SUMMARY OF THE INVENTION

According to the cutting apparatus, although it is possible to cut a scheduled division line with high accuracy, there is a problem that, while it performs a cutting process along a scheduled division line, a crack sometimes appears in a processing region by the cutting blade and damages a plurality of devices.

As a result of earnest examination conducted by the applicant in order to solve the problem just described, it has been found that the problem is caused by the fact that, where a crack potentially exists in the inside of a wafer in advance, when processing by a cutting blade comes to the crack at an angle proximate to a direction in which the crack extends, the crack is grown by the processing and, when the grown crack reaches a device in an adjacent region, damage to the device is increased.

Therefore, it is an object of the present invention to provide a processing method for a wafer by which, when a wafer is cut by a cutting blade of a cutting apparatus to divide the wafer into individual device chips, even if a crack potentially exists in the inside of the wafer in advance, a plurality of devices are suppressed from being damaged by further growth of the crack.

In accordance with an aspect of the present invention, there is provided a processing method for a wafer by which a wafer having a plurality of devices formed on a surface thereof and partitioned in a lattice pattern by scheduled division lines formed in a first direction and scheduled division lines formed in a second direction orthogonal to the first direction is divided into individual device chips by a cutting blade. The processing method includes a crack detection step for irradiating illumination of a wavelength having transparency with respect to the wafer from a side face of the wafer, picking up an image of the wafer by image pickup means positioned with respect to the wafer, and detecting whether or not a crack is generated in an inside of the wafer, a crack direction verification step for verifying, when it is detected by the crack detection step that a crack is generated in the inside of the wafer, to which one of the first direction and the second direction a direction in which the crack extends is nearer, a first cutting step for positioning the cutting blade to a scheduled division line of a direction decided to be a direction farther from the direction in which the crack extends from between the first direction and the second direction by the crack direction verification step and cutting the scheduled division line, and a second cutting step for positioning, after the first cutting step ends, the cutting blade to a scheduled division line of a direction decided to be nearer to the direction in which the crack extends and cutting the scheduled division line.

According to the processing method for a wafer of the present invention, where a crack potentially exists in the inside of a wafer in advance, if the scheduled division lines in the direction farther from the direction in which a crack extends are cut first, then the crack is divided in the direction in which the crack extends, and thereafter, the cutting blade is positioned to the scheduled division line of the direction nearer to the direction in which the crack extends and the scheduled division line is cut. Therefore, even if the processing by the cutting blade comes to the crack from the direction nearer to the direction in which the crack extends, since the crack is divided already, the growth of the crack at the division location is blocked, and further increase of damage to the device is suppressed.

The above and other objects, features and advantages of the present invention and the manner of realizing them will become more apparent, and the invention itself will best be understood from a study of the following description and appended claim with reference to the attached drawings showing a preferred embodiment of the invention.

DETAILED DESCRIPTION OF THE PREFERRED EMBODIMENT

Figure 1:
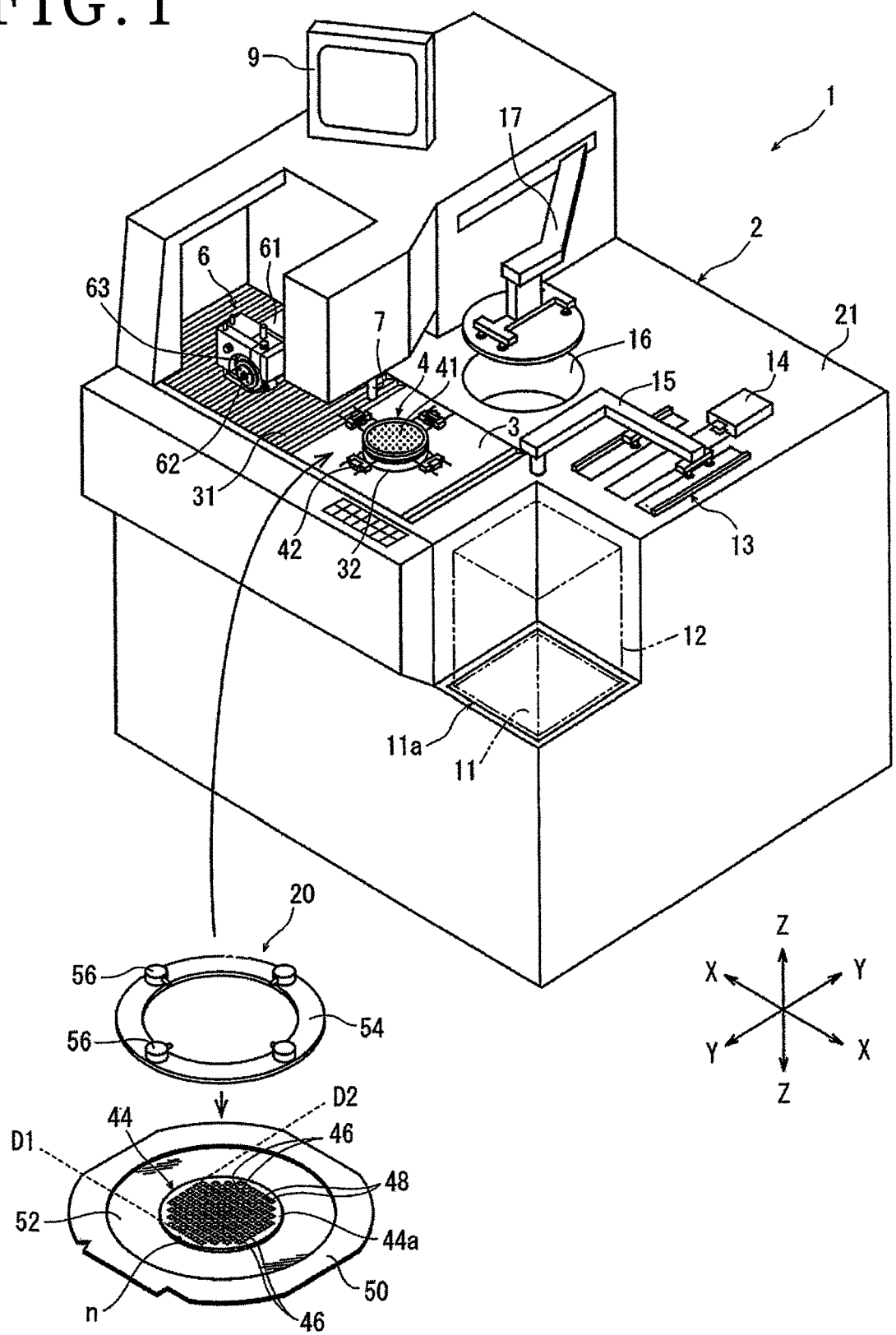
FIG. 1 is a general perspective view of a cutting apparatus suitable for carrying out a processing method of the present invention.

In the following, an embodiment of a processing method for a wafer configured on the basis of the present invention is described in detail with reference to the accompanying drawings. FIG. 1 depicts a general perspective view of a cutting apparatus that can carry out the processing method for a wafer configured in accordance with the present invention. A cutting apparatus 1 in the present embodiment includes an apparatus housing 2 of a substantially rectangular parallelepiped. In the apparatus housing 2, a cover table 3 and a chuck table 4 for holding a workpiece thereon are disposed for movement in a direction indicated by an arrow mark X that is a cutting feeding direction. The cover table 3 includes bellows 31 in the X direction and has an opening 32 formed at a central location thereof. The chuck table 4 is fitted in the opening 32 and disposed for rotation by a rotating mechanism not depicted. Four clamps 42 are disposed at distances of 90 degrees on the chuck table 4 such that they surround the chuck table 4, and are rotated integrally with the chuck table 4. The chuck table 4 has an absorption chuck 41 disposed on an upper face thereof such that, when suction means not depicted is rendered operative, a workpiece is sucked to and held by a holding face that is an upper face of the absorption chuck 41. The cover table 3 and the chuck table 4 configured in such a manner as described above are moved in the cutting feeding direction indicated by the arrow mark X by cutting feeding means not depicted. On an upper face of the apparatus housing 2, display means 9 is provided uprightly such that various kinds of information are displayed thereon on the basis of a signal from control means hereinafter described, and work information, an image and position information of a potential crack hereinafter described and so forth are displayed on the display means 9.

The cutting apparatus 1 in the present embodiment includes a spindle unit 6 as cutting means. The spindle unit 6 is mounted on the apparatus housing 2 and includes a spindle housing 61 that is moved and adjusted in a direction indicated by an arrow mark Y that is an indexing direction and another arrow mark Z that is a cut-in direction, a rotational spindle 62 supported for rotation on the spindle housing 61, and a cutting blade 63 mounted at a front end portion of the rotational spindle 62. As the cutting blade 63, an electroformed blade is used which is formed by coupling abrasive grain to a side face of a base formed from aluminum or the like by metal plating of nickel or the like. The spindle unit 6 as the cutting means configured in this manner is moved in the indexing feeding direction indicated by the arrow mark Y in FIG. 1 by indexing feeding means not depicted and is moved in the cut-in feeding direction indicated by the arrow mark Z in FIG. 1 by cut-in feeding means not depicted.

Figure 2:
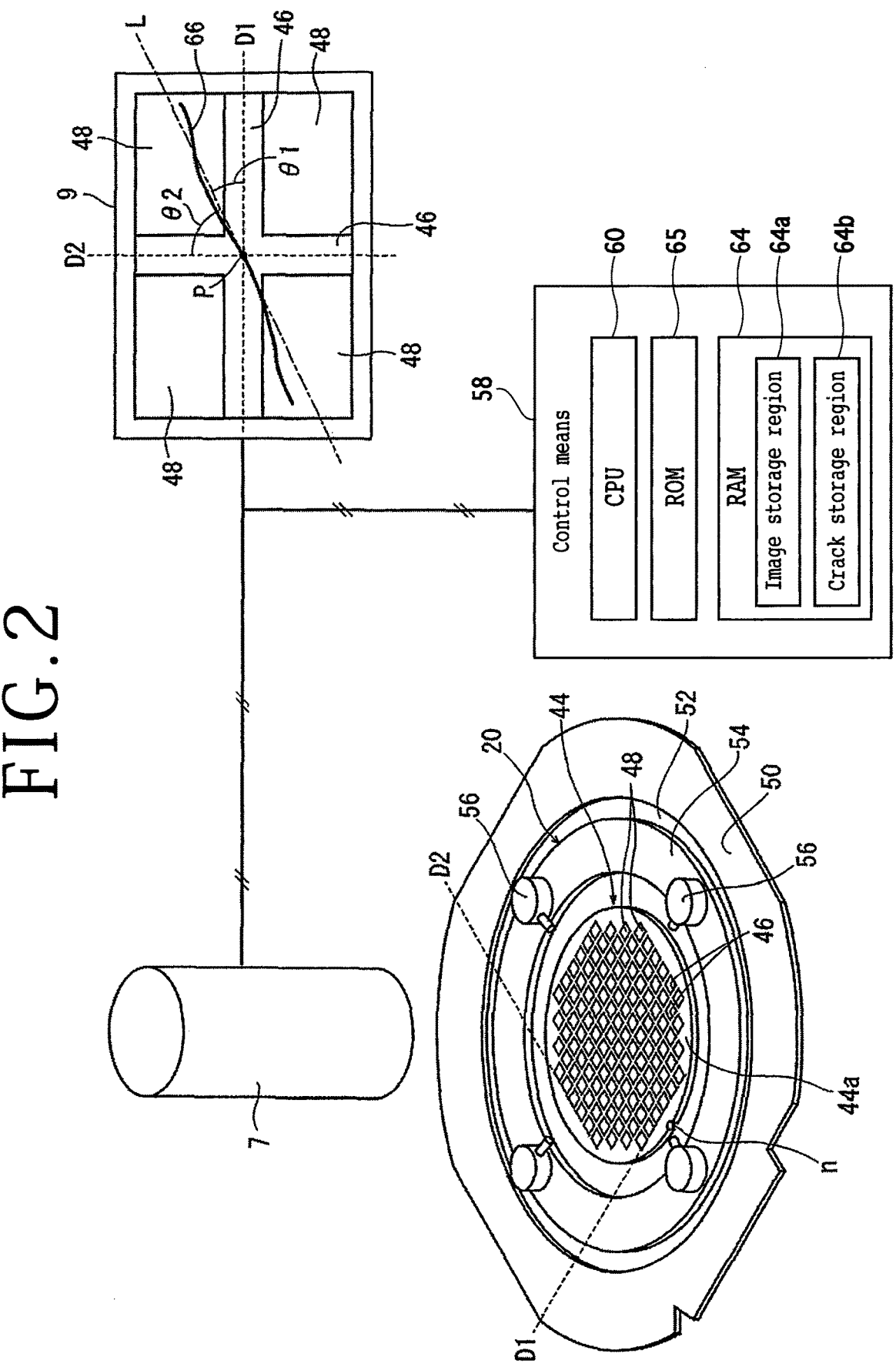
FIG. 2 is a schematic view illustrating a crack detection step executed by the cutting apparatus depicted in FIG. 1.

The cutting apparatus 1 in the present embodiment includes image pickup means 7 for picking up an image of the surface of a workpiece, for example, a wafer, held on the chuck table 4 to detect a region to be cut by the cutting blade 63 and picking up an image of the inside of the wafer. The image pickup means 7 is configured from an ordinary image pickup element (charge-coupled device (CCD)) that picks up an image of the surface of the wafer using visible rays, an optical system for capturing infrared rays, and another image pickup element (infrared CCD) for outputting an electric signal corresponding to the infrared rays captured by the optical system. Picked up image information is sent to control means 58 hereinafter described (refer to FIG. 2). As depicted in FIG. 2, the control means 58 is connected at least to the image pickup means 7 and the display means 9. Further, the control means 58 is connected also to moving means not depicted (cutting feeding means, indexing feeding means, cut-in feeding means and so forth) for moving the chuck table 4 and the spindle unit 6. The control means 58 is configured from a computer and includes a central processing unit (CPU) 60 that performs arithmetically processing in accordance with a control program, a read-only memory (ROM) 65 in which the control program and so forth are stored therein, a readable-writable random access memory (RAM) 64 for temporarily storing detected information, an arithmetic operation result and so forth, an input interface, and an output interface. To part of a storage region of the random access memory 64, an image storage region 64a for storing images picked up by the image pickup means 7 and a crack storage region 64b for storing crack information such as a position of a crack detected from within the picked up images, a direction in which the crack extends and so forth are set (a detailed illustration thereof is omitted). It is to be noted that the control means 58 executes also control programs for operating the moving means (cutting feeding means, indexing feeding means, cut-in feeding means and so forth) configuring the cutting apparatus 1 and other operation units.

In a cassette placement region 11a of the apparatus housing 2, a cassette placement table 11 is disposed which receives a cassette, in which a wafer is accommodated, placed thereon. The cassette placement table 11 is configured for movement in an upward and downward direction by lifting means not depicted. A cassette 12 in which wafers are accommodated is placed on the cassette placement table 11. The apparatus housing 2 further includes delivery means 14 for delivering a wafer accommodated in the cassette 12 placed on the cassette placement table 11 to a temporary placement table 13, first transport means 15 for transporting the wafer delivered to the temporary placement table 13 to the chuck table 4, washing means 16 for washing the wafer cut and processed on the chuck table 4, and second transport means 17 for transporting the wafer cut and processed on the chuck table 4 to the washing means 16.

FIG. 1 further depicts a wafer 44 to be processed by the cutting apparatus 1 described hereinabove, and illumination means 20 used when it is to be detected whether or not a crack is generated in the inside of the wafer 44. A front face 44a of the wafer 44 of a disk shape that can be formed from Si (silicon) or the like is partitioned into a plurality of rectangular regions by lattice-like scheduled division lines 46, and a device 48 is formed in each of the plurality of rectangular regions. A notch n indicative of a crystal orientation of the wafer 44 is formed on an outer peripheral portion of the wafer 44, and the scheduled division lines 46 are set to a direction (first direction) D1 orthogonal to a straight line that interconnects the center of the wafer 44 and the notch n and another direction (second direction) D2 orthogonal to the first direction D1. The front face 44a of the wafer 44 is partitioned in a lattice pattern by the scheduled division lines 46, and a device 48 is formed in each of the partitioned regions. In the present embodiment, the wafer 44 is adhered at a rear face thereof to an adhesive tape 52 fixed at a circumferential edge thereof to an annular frame 50. It is to be noted that the illumination means 20 includes an annular plate 54 having an inner diameter greater than the diameter of the wafer 44 and a plurality of (in the present embodiment, four) light sources 56 disposed at distances in a circumferential direction on the upper face of the annular plate 54. It is advantageous that the outer diameter of the annular plate 54 is smaller than the inner diameter of the annular frame 50. The light sources 56 for irradiating light toward the inner side in a diametrical direction of the annular plate 54 irradiate light of a wavelength having transparency with respect to the wafer 44. For example, where the wafer 44 is of Si (silicon), light to be irradiated from the light sources 56 is selected such that it has a wavelength of 1064 to 3000 nm having transparency with respect to Si (silicon). The cutting apparatus 1 of the present embodiment generally has such a configuration as described above, and the processing method for a wafer implemented by the cutting apparatus 1 is described below.

When the cutting apparatus 1 is used to process a wafer 44, a crack detection step is carried out first. In order to carry out the crack detection step, a wafer 44 that is to be made a processing target is transported from the cassette 12 by the transport means 14 and 15 described above. Then, the wafer 44 pasted to the adhesive tape 52 is placed on the upper face of the chuck table 4 with the rear face of the wafer 44 directed downwardly. Then, the suction means not depicted is rendered operative to cause the absorption chuck 41 of the chuck table 4 to generate suction force to absorb the wafer 44 to the absorption chuck 41. Further, the annular frame 50 is fixed at a circumferential edge portion thereof by the clamps 42. Then, as depicted in FIG. 1, the illumination means 20 is disposed between the outer periphery of the wafer 44 and the inner periphery of the annular frame 50 such that light of a wavelength (for example, 1064 nm) having transparency with respect to the wafer 44 is irradiated from the outer periphery side of the wafer 44 from the light sources 56 of the illumination means 20. Then, in order to oppose the wafer 44 to the image pickup means 7, the chuck table 4 is moved by the moving means not depicted. Then, while the chuck table 4 is moved by the moving means, an image of the entire wafer 44 is picked up by the image pickup means 7. In this manner, while light of a wavelength having transparency with respect to the wafer 44 is irradiated from the outer periphery side of the wafer 44, an image of the wafer 44 is picked up by the image pickup means 7 disposed in an opposing relationship to the wafer 44. By this, an image of a crack existing in the wafer 44 can be picked up.

Since an image picked up by the image pickup means 7 is displayed on the display means 9 as depicted in FIG. 2, if a crack exists, then the crack (denoted by reference numeral 66) of the wafer 44 can be detected on the basis of the image display on the display means 9. When the crack 66 is detected, image information obtained by the image pickup of the region in which the crack 66 is included is stored into the image storage region 64a of the random access memory 64 of the control means 58, and position information of the crack 66 and information of a direction (angle) L in which the crack 66 extends are stored in a linked relationship with the image information into the crack storage region 64b. It is to be noted that, as regards a specification method of the direction L in which the crack 66 extends, preferably the direction L is specified by an angle at a position (indicated by a point P) at which the direction L crosses a scheduled division line 46 to be cut, for example, by the cutting blade 63. However, the present invention is not limited to this, and the direction L may be specified depending upon an average direction (angle) of the entire crack 66.

After the generation position of the crack 66 described above and the direction L in which the crack 66 extends are specified, a crack direction verification step for performing comparison between the direction L and the first direction D1 defined on the wafer 44 and between the direction L and the second direction D2 to decide to which one of the first direction D1 and the second direction D2 the direction L in which the crack 66 extends is nearer. More particularly, an angle ($\theta 1$) formed by the first direction D1 and the direction L in which the crack 66 extends and another angle ($\theta 2$) formed by the second direction D2 and the direction L in which the crack 66 extends are specified as depicted on the display means 9 in FIG. 2. As a result of the comparison between the angles $\theta 1$ and $\theta 2$ (in the present embodiment, $\theta 1 < \theta 2$), it is verified that the first direction D1 is nearer to the direction L in which the crack 66 extends and the second direction D2 is farther from the direction L in which the crack 66 extends. Then, the verification result is stored into the crack storage region 64b of the control means 58 together with the information of the crack 66 described above. The crack direction verification result is completed in this manner.

After the crack direction verification step is completed, a cutting step for cutting the wafer 44 is carried out. If no crack is found at the crack detection step described above, then it is free to decide in which one of the first direction D1 and the second direction D2 the scheduled division lines 46 are to be cut first, and the chuck table 4 is moved in the X direction indicated by the arrow mark X in FIG. 1, namely, in the cutting feeding direction, to cut a scheduled division line 46 using the cutting blade 63 and, while an indexing feeding operation of the spindle unit 6 in the Y direction is interposed, all scheduled division lines 46 formed along the first direction D1 on the wafer 44 are cut. Then, the chuck table 4 is rotated by 90 degrees such that the scheduled division lines 46 formed along the second direction D2 of the wafer 44 are aligned with the direction indicated by X in FIG. 1, and then a cutting operation similar to that described above is executed to cut all of the scheduled division lines 46. The cutting step for the wafer 44 is completed thereby.

Figure 3A:
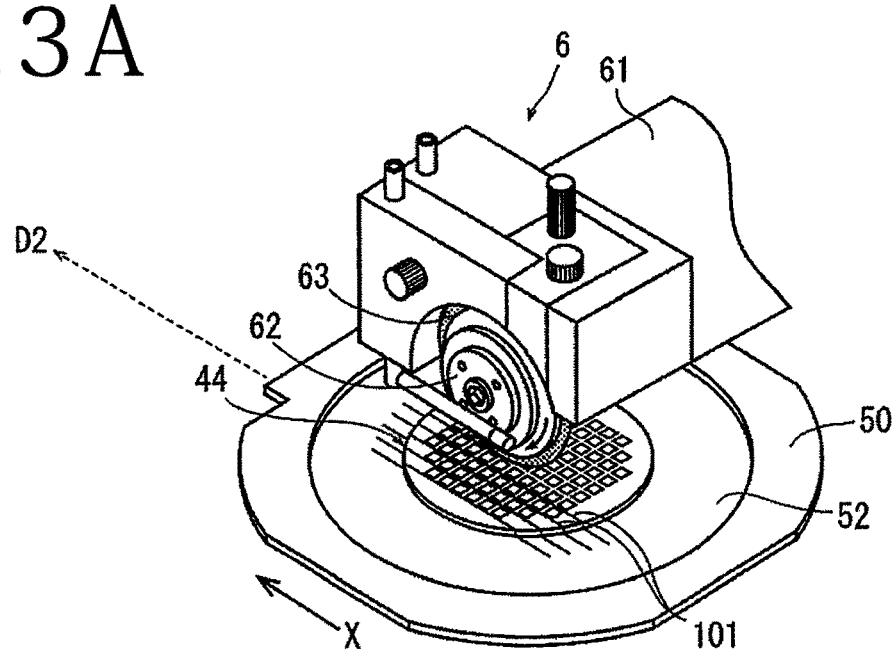
FIGS. 3A to 3C are perspective views illustrating a first cutting step and a second cutting step in the wafer processing method of the present invention.

If, in contrast to the cutting step when no crack is found in the wafer 44 as described above, a crack 66 is found in the wafer 44 at the crack detection step, then the cutting step is divided into a first cutting step and a second cutting step, which are carried out successively. The "first cutting step" and the "second cutting step" are defined as a "first cutting step for positioning the cutting blade to a scheduled division line of a direction decided as a direction farther from the direction L in which the crack extends from between the first direction D1 and the second direction D2 and cutting the scheduled division line" and a "second cutting step for positioning, after the first cutting step comes to an end, the cutting blade to a scheduled division line of a direction decided to be nearer to the direction L in which the crack extends." In the present embodiment, the direction decided to be farther from the direction L in which the crack 66 extends at the crack direction verification step described above is the second direction D2, and the first direction D1 is decided and stored as a direction nearer to the direction L in which the crack 66 extends. Therefore, at the cutting step in the present embodiment, cutting for the scheduled division lines 46 formed along the second direction D2 is carried out first (first cutting step) as depicted in FIG. 3A, and then all of the scheduled division lines 46 formed in the second direction D2 are cut.

Figure 3B:
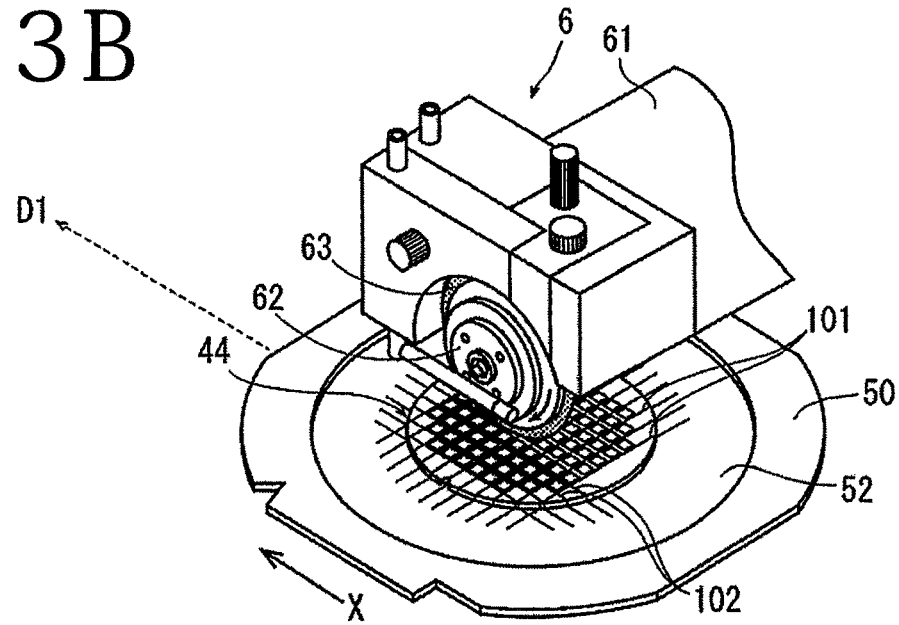
Figure 3C:
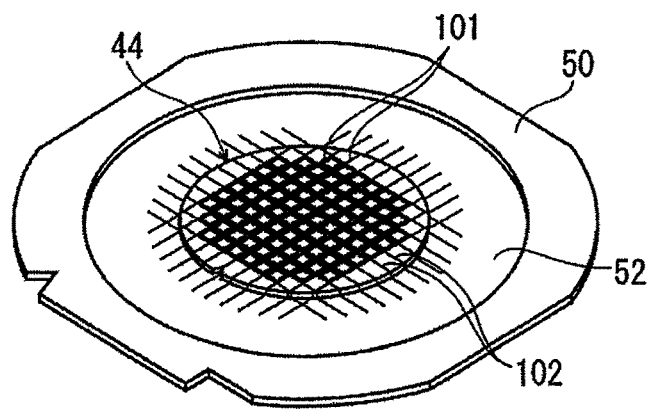

Then, after the first cutting step is carried out, cutting for the scheduled division lines 46 formed along the first direction D1 orthogonal to the second direction D2 is carried out (second cutting step) as depicted in FIG. 3B, and by executing cutting for all scheduled division lines 46, the cutting step is completed (refer to FIG. 3C). If a crack 66 is found at the crack verification step, then by successively executing such a first cutting step and a second cutting step as described above, the scheduled division lines in a direction farther from a direction in which a crack extends are cut first. Consequently, the crack is cut by cutting from a direction in which a crack is less likely to grow, and even if the cutting blade is positioned to a scheduled division line of a direction that defines an angle nearer to the direction in which the crack extends and the scheduled division line is cut, since the crack 66 is divided already, the growth of the crack at the division location is blocked, and further increase of damage to the device is suppressed.

The present invention is not limited to the embodiment described above and various modifications are possible without departing from the technical scope of the present invention. For example, while, in the embodiment described above, the illumination means 20 in which the light sources 56 is disposed on the annular frame 50 is used in order to detect a crack, the present invention is not limited to this, and illumination means may be disposed on the cutting apparatus 1 such that light of a wavelength having transparency with respect to the wafer 44 is irradiated from a side.

Further, while, in the embodiment described above, the rear face side of the wafer 44 is pasted to the adhesive tape 52 and held on the chuck table 4 with the front face 44a side of the wafer 44 directed upwardly to carry out cutting, the present invention is not limited to this and may be applied to a case in which the wafer 44 is pasted at the front face 44a thereof to the adhesive tape 52 and held on the chuck table 4 with the rear face side thereof directed upwardly to carry out cutting.

Furthermore, while it is described in the foregoing description that, in the above-described embodiment, a wafer 44 of Si (silicon) is presented as a workpiece and the crack detection step for irradiating infrared rays to detect a crack using an infrared CCD is carried out, the present invention is not limited to this, and also it is possible to apply the present invention to a workpiece configured from other materials. Thus, if a wafer can pass visible rays therethrough, then there is no necessity to dispose an infrared CCD, and image pickup means that is used for alignment or the like may be adopted as it is to carry out the crack detection step.

The present invention is not limited to the details of the above described preferred embodiment. The scope of the invention is defined by the appended claim and all changes and modifications as fall within the equivalence of the scope of the claim are therefore to be embraced by the invention.

What is claimed is:

1. A processing method for a wafer by which a wafer having a plurality of devices formed on a surface thereof and partitioned in a lattice pattern by scheduled division lines formed in a first direction and scheduled division lines formed in a second direction orthogonal to the first direction is divided into individual device chips by a cutting blade, the processing method comprising:
    a crack detection step for irradiating illumination of a wavelength having transparency with respect to the wafer from a side face of the wafer, picking up an image of the wafer by image pickup means positioned with respect to the wafer, and detecting whether or not a crack is generated in an inside of the wafer, said crack detection step being performed for the wafer having not undergone a cutting process;
    a crack direction verification step for verifying, when it is detected by the crack detection step that a crack is generated in the inside of the wafer, to which one of the first direction and the second direction a direction in which the crack extends is nearer;
    a first cutting step for positioning the cutting blade to a scheduled division line of a direction decided to be a direction farther from the direction in which the crack extends from between the first direction and the second direction by the crack direction verification step and cutting the scheduled division line; and
    a second cutting step for positioning, after the first cutting step ends, the cutting blade to a scheduled division line of a direction decided to be nearer to the direction in which the crack extends and cutting the scheduled division line.

2. The method of claim 1 wherein the side face of the wafer comprises an outer periphery side of the wafer.

3. The method of claim 1 wherein the image pickup means comprises at least one charge-coupled device.

4. The method of claim 1 wherein the image pickup means comprises a charge coupled device, an optical system, and an infrared charge coupled device.

5. The method of claim 1 wherein verifying to which one of the first direction and the second direction a direction in which the crack extends is nearer comprises comparing a first angle formed by the first direction and a direction of the crack with a second angle formed by the second direction and the direction of the crack.

6. The method of claim 1 wherein the irradiating illumination comprises infrared rays.

7. The method of claim 1 wherein the irradiating illumination comprises visible rays.

8. A processing method for a wafer by which a wafer having a plurality of devices formed on a surface thereof and partitioned in a lattice pattern by scheduled division lines formed in a first direction and scheduled division lines formed in a second direction orthogonal to the first direction is divided into individual device chips by a cutting blade, the processing method comprising:
    irradiating the wafer with illumination of a wavelength having transparency with respect to the wafer from a side face of the wafer, picking up an image of the wafer, and detecting whether or not a crack is generated in an inside of the wafer before cutting the wafer;
    verifying to which one of the first direction and the second direction a direction in which the crack extends is nearer when it is detected that a crack is generated in the inside of the wafer;
    positioning the cutting blade to a scheduled division line of a direction decided to be a direction farther from the direction in which the crack extends from between the first direction and the second direction and cutting the scheduled division line; and
    after the first cutting step ends, positioning the cutting blade to a scheduled division line of a direction decided to be nearer to the direction in which the crack extends and cutting the scheduled division line.

9. The method of claim 8 wherein the side face of the wafer comprises an outer periphery side of the wafer.

10. The method of claim 8 wherein the image is picked up using at least one charge-coupled device.

11. The method of claim 8 wherein the image is picked up using a charge coupled device, an optical system, and an infrared charge coupled device.

12. The method of claim 8 wherein verifying to which one of the first direction and the second direction a direction in which the crack extends is nearer comprises comparing a first angle formed by the first direction and a direction of the crack with a second angle formed by the second direction and the direction of the crack.

13. The method of claim 8 wherein the illumination comprises infrared rays.

14. The method of claim 8 wherein the illumination comprises visible rays.

* * * * *